(12) United States Patent
Nilsen

(10) Patent No.: US 6,274,723 B1
(45) Date of Patent: Aug. 14, 2001

(54) DENDRITIC NUCLEIC ACIDS EXHIBITING MAXIMAL SELF-ASSEMBLY

(75) Inventor: Thor W. Nilsen, Haddonfield, NJ (US)

(73) Assignee: Polyprobe, Inc., Philadelphia, PA (US)

( * ) Notice: Subject to any disclaimer, the term of this patent is extended or adjusted under 35 U.S.C. 154(b) by 0 days.

(21) Appl. No.: 09/492,471

(22) Filed: Jan. 27, 2000

Related U.S. Application Data

(63) Continuation of application No. PCT/US98/15764, filed on Jul. 29, 1998.
(60) Provisional application No. 60/054,020, filed on Jul. 29, 1997.
(51) Int. Cl.[7] ............... C12Q 1/68; C07H 21/00; C07H 21/02; C07H 19/00
(52) U.S. Cl. ............ 536/24.3; 536/22.1; 536/2; 536/23.1; 536/25.3; 435/6; 435/91.1; 435/91.2
(58) Field of Search ............ 435/6, 91.1, 91.2; 536/22.1, 23.1, 24.3, 25.3

(56) References Cited

U.S. PATENT DOCUMENTS

| | | | |
|---|---|---|---|
| 5,175,270 | 12/1992 | Nilsen et al. | 536/27 |
| 5,484,904 | 1/1996 | Nilsen et al. | 536/23.1 |
| 5,487,973 | 1/1996 | Nilsen et al. | 435/6 |
| 5,561,043 | 10/1996 | Cantor et al. | 435/6 |

OTHER PUBLICATIONS

Hudson, et al., Am. Chem. Soc., 115:2119–2124 (1993).

*Primary Examiner*—Jezia Riley
(74) *Attorney, Agent, or Firm*—Lerner, David, Littenberg, Krumholz & Mentlik, LLP

(57) ABSTRACT

Disclosed are nucleic acid matrices comprising a dendrimeric network of interconnected monomers. Each monomeric unit is synthesized using nucleic acid sequences having no repeats of subsequences of a predetermined length. In preferred embodiments, the subsequences have a length of 3–5 nucleotides. The DNA monomers assembled therefrom exhibit maximal self-assembly properties in that they hybridize substantially only to portions of other monomers having complementary sequences. The monomers in the dendrimeric assembly may be cross-linked to enhance structural integrity of the matrix.

12 Claims, 7 Drawing Sheets

STRAND 1
seq1 (+)$_n$ = seq1 (+) seq1 (+) seq1 (+) seq1 (+)

STRAND 2
seq1 (-) seq2 (+)$_n$ = seq1 (-) seq2 (+) seq2 (+) seq2 (+)

STRAND 3
seq2 (-) seq3 (+)$_n$ = seq2 (-) seq3 (+) seq3 (+) seq3 (+)

STRAND 4
seq3 (-) seq1 (+)$_n$ = seq3 (-) seq1 (+) seq1 (+) seq1 (+)

SINGLE
STRAND1 (+) = (seq1 (+))$_n$ (seq2 (-))

WHERE n=3:

seq1 (+)  seq1 (+)  seq1 (+)  seq2 (-)

1 LAYER
"IDEAL"

SINGLE
STRAND2 (+) = (seq2 (+))$_n$ (seq1 (-))

WHERE n=3:

seq2 (+)  seq2 (+)  seq2 (+)  seq1 (-)

2 LAYER
"IDEAL"

DENDRITIC NUCLEIC ACIDS EXHIBITING MAXIMAL SELF-ASSEMBLY

CROSS-REFERENCE TO RELATED APPLICATIONS

This application is a continuation of PCT US/98/15764, filed Jul. 29, 1998, which in turn claims priority under 35 U.S.C. §119(e) from the U.S. Provisional Application No. 60/054,020, filed Jul. 29, 1997 abandoned.

BACKGROUND OF THE INVENTION

The present invention relates to methods for the detection of nucleic acids, and more particularly to labeled carriers for probes that hybridize to the nucleic acid of interest.

BACKGROUND OF THE INVENTION

Dendritic molecules are highly-branched arborescent structures and have found applications as chemical reagents, lubricants, contrast media for magnetic resonance, and others. See, e.g., Barth et al., Bioconjugate Chemistry 5:58–66 (1994); Gitsov & Frechet, Macromolecules 26:6536–6546 (1993); Hawker & Frechet, J. Amer. Chem. Soc. 112:7638–7647 (1990a); Hawker & Frechet, Macromolecules 23:4726–4729 (1990b); Hawker et al., J. Chem. Soc. Perkin Trans. 1:1287–1297 (1993); Lochmann et al. J. Amer. Chem. Soc. 115:7043–7044 (1993); Miller et al., J. Amer. Chem. Soc. 114:1018–1025 (1992); Mousy et al., Macromolecules 25:2401–2406 (1992); Naylor et al., J. Amer. Chem. Soc. 111:2339–2341 (1989); Spindler & Frechet, Macromolecules Macromolecules 26:4809–4813 (1993); Turner et al., Macromolecules 26:4617–4623 (1993); Wiener et al., Magnetic Resonance Med. 31(1):1–8 (1994); Service, 267:458–459 (1995); Tomalia, Sci. Amer. 62–66 (1995); and U.S. Pat. Nos. 4,558,120; 4,507,466; 4,568,737; 4,587,329; 4,857,599; 5,527,524; and 5,338,532 to Tomalia. Dendritic molecules offer several advantages over other molecular architectures. First, dendrimers contact the maximum volume or area with a minimum of structural elements. Second, the growth of dendritic molecules can be highly controlled to yield molecules of ideal size and molecular weight. Finally, the large number of defined "ends" can be derivatized to yield highly labeled molecules with defined spacing between the labels.

Nucleic acid dendrimers have been constructed following the technology that Tomalia applied to conventional organic polymers. See Hudson et al., "Nucleic Acid Dendrimers: Novel Biopolymer Structures," Am. Chem. Soc. 115:2119–2124 (1993); and U.S. Pat. No. 5,561,043 to Cantor.

DNA detection is typically achieved with an absorption measurement where the quantity of DNA is directly proportional to the absorbance of solution. Though this technique is moderately sensitive, it provides no information about the specific sequence of DNA, only how much DNA is present. DNA can also be labeled with fluorescent, radioactive or chemiluminescent molecules. Labeling offers the advantages of increased detection sensitivity and specificity. The specificity comes from only labeling the desired pieces of DNA. The greatest use of this labeling for DNA detection is by labeling a complementary probe to the target DNA. If the labeled probe hybridizes to its target and can be detected, one can infer that the target is present. The most common use of this technique is called Southern blotting where DNA-DNA targets are detected after hybridization to a labeled probe. Dendritic nucleic acids are useful for the development of nucleic acid diagnostics as signal amplification tools. Due the relatively large size of nucleic acid molecules, nucleic acid dendrimers are readily labeled with numerous fluorescent compounds and/or protein moieties with limited steric hindrance and/or quenching. They also show potential as drug (antisense) delivery vehicles.

Perhaps the most commonly used detection method for DNA relies on amplification of the DNA rather than adding a label. This technique for amplification is called the polymerase chain reaction (PCR). In this technique, the target strand is amplified in situ by the addition of deoxynucleotide triphosphates of all four bases, a thermally stable polymerase and a primer DNA which is a short strand complementary to target. The primer (or primers) mark the point of duplication (and the point of termination). If a single primer is used the complementary strand will be copied to the termination, but more commonly two primers are used to indicate the beginning and end of the amplified sequence. Detection of the amplified DNA can be achieved by any of a number of techniques. Perhaps the most common method entails separating the amplified DNA by electrophoresis (typically in agarose or polyacrylamide, though capillary electrophoresis has also been used) and detecting it by staining with a fluorescent intercalating reagent (usually ethidium bromide). The PCR technique therefore allows for both increased sensitivity and specificity.

Nucleic acid matrices assembled substantially upon nucleic acid hybridization and which are characterized by dentritic-type architecture, but yet structurally distinct from the aforementioned organic and nucleic acid dendrimers, are taught in U.S. Pat. Nos. 5,175,270; 5,484,904; and 5,487,973 to Nilsen et al., and assigned to Polyprobe, Inc. The unique molecular design of Polyprobe's matrices accommodates a large number of labels, resulting in more than a 100-fold amplification of the signal compared to various prior art methods—target nucleic acids can be detected even when present in the sample in extremely small (e.g., femptogram ($10^{-15}$)) amounts. Thus, Polyprobe's technology represents a significant improvement over state-of-the-art nucleic acid detection methods, most notably PCR.

SUMMARY OF THE INVENTION

The present invention is directed to an improvement of the nucleic acid dendrimers described in the aforementioned Nilsen patents, and which exhibit maximal self-assembly. One aspect of the present invention provides a dendritic polynucleotide having a plurality of single stranded hybridization arms; said polynucleotide comprising a plurality of polynucleotide monomers bonded together by hybridization; each polynucleotide monomer having an intermediate region comprising a linear, double stranded waist region having a first end and a second end, said first end terminating with two single stranded hybridization regions, each from one strand of the waist region, and said second end terminating with one or two single stranded hybridization regions, each from one strand of the waist region; and in said dendritic polynucleotide each polynucleotide monomer is hybridization bonded to at least one other polynucleotide monomer at at least one such hybridization region;

and wherein each of said hybridization regions and said waist regions of said plurality of monomers comprise sequences containing no repeats of subsequences having X nucleotides, wherein X is an integer of at least 2. In preferred embodiments, X is an integer from 2 to about 7; in more preferred embodiments, X is 3, 4 or 5.

The nature and constitution of the DNAs that comprise the monomers allow for extremely precise and controlled assembly, e.g., maximal self-assembly, of the nucleic acid dendritic matrices of the invention. That is, the hybridization regions of a given monomer hybridize substantially only with a substantially complementary hybridization region of another monomer. Therefore, self-hybridization is reduced, preferably to the extent that it is negligible. The advantages are that interference with the assay is reduced, leading to greater accuracy and sensitivity.

Compositions, kits and methods of making and using the polynucleotides are also described.

DETAILED DESCRIPTION OF THE INVENTION

Ideally, a dendritic nucleic acid structure will be highly branched at relatively low molecular weight, have multiple sequence specificities, be composed of only a few single strands, have predictable controlled growth, and minimize steric hindrance for the addition of monomers. Nucleic acid dendrimers may be assembled via hybridization using as few as two single stranded molecules. However, the use of seven single stranded molecules is preferred because it yields a structure with many desirable features. Various configurations of nucleic acid molecules can give rise to large dendritic structures. The particular structures described herein represent a balance among complexity of Ireagents, their ease of synthesis, and the rate of geometric growth of the dendrimer with each additional layer via hybridization.

In the disclosed structures, an initiating dendrimer monomer which is a heterodimer of two partially single stranded nucleic acid molecules with two a(+) and two c(+) single stranded regions, provides four arms to which the first layer of four dendrimer monomers hybridize (See FIGS. 1 and 2). Like the initiator, first layer dendrimer monomers also have four single-stranded regions, a single (−) sequence, either a(−) or c(−), and three (+) sequences, either d(+) or e(+). The second layer monomers are similar to the initiator and first layer monomers, except the (−) sequence is either d(−) or e(−) and the (+) sequences are either a(+) or c(+). Thus, from the initiator which has a(+) and c(+) sequences, the first layer is added generating the 1-layer dendrimer with d(+) and e(+) sequences. The addition of the second layer regenerates the a(+) and c(+) sequences, thereby allowing the geometric assembly of the dendritic structure by alternate hybridization of dendrimer monomers. By the forth layer, the assembly will produce molecules with 324 single stranded (ss) arms regions, 2,916 ss regions by the sixth layer, and 26,244 ss regions by the eighth layer.

Figure 1A:
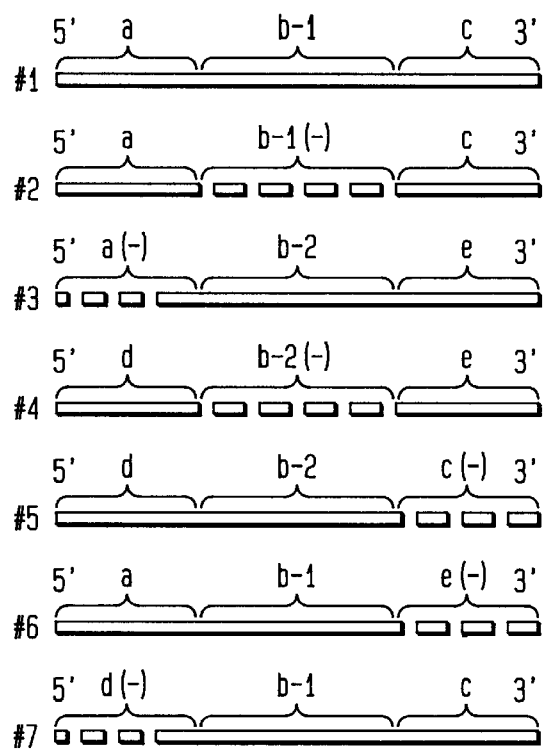
FIG. 1A is a schematic diagram of a preferred embodiment of the present invention, namely seven unique single-stranded nucleic acid oligomers used to assemble the instant nucleic acid monomers. The solid lines depict "+" strand and the broken lines depict "−" strand sequences.

FIG. 1a depicts the seven single-stranded nucleic acid oligomers used for the assembly of preferred dendritic or matrix monomers. These seven molecules in toto, are comprised of six oligomeric sequences—four arm sequences and two waist sequences. Each lettered segment (a,b,c,d,e) denotes one of the unique sequences on the different oligomers. For each oligomer depicted, the solid lines represent "+" (positive) strands and the broken lines represent "−" (negative) or complementary strand sequences. Each of the sequences (a,b,c,d,e) is designed so as to have minimal sequence similarity to each other.

Figure 1B:
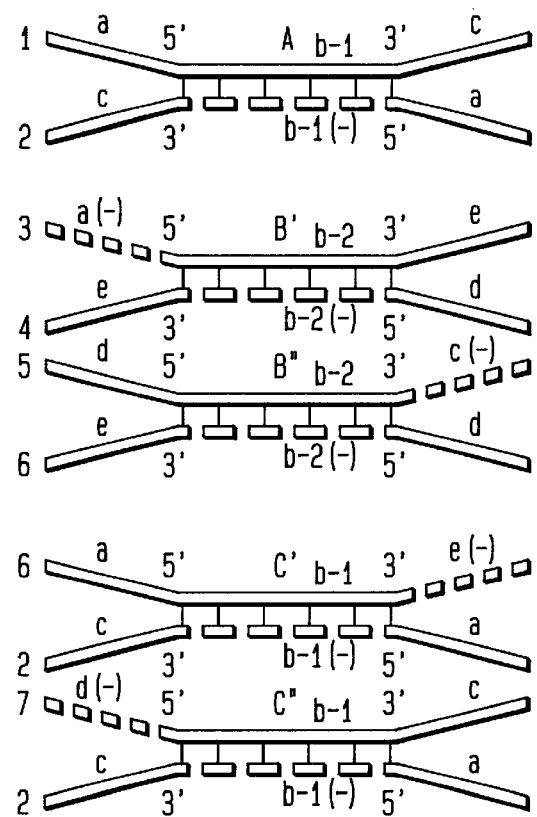
FIG. 1B depicts the heterodimers (dendrimer monomers) that are used as building blocks for nucleic acid dendrimer assembly. Heterodimer A is a core monomer since the arms of heterodimers B' and B" can anneal to A. In turn, the arms of C' and C" can anneal to the three arms of B' and B".

As shown in FIG. 1b, the monomers A, B', B", C', and C" are the repeat units of the structure and are called dendrimer monomers. Monomers are assembled from the seven single stranded reagents illustrated in FIG. 1A. The initiator, or "A" monomer is ss1(+) hybridized to ss2(+). The A monomer has four single-stranded arms each complementary to one of the single-stranded arms of monomers B' and B". Strand number 4 is the (−) waist strand for both B type monomers. Strand 4 is annealed to either strands #3 (for B') or strand #5 (for B"). The B' monomer can anneal to two of the arms of the A monomer, the initiator, while B" can anneal to the other two arms of the initiator A monomer. Site-saturating annealing to the ss arms of one A monomer to 4 B-type monomers forms the 1-layer dendritic structure illustrated in FIG. 2A. No other hybridization is possible when the proposed sequence of steps is followed. Together, B' and B" monomers saturate all available hybridization sites of the initiator A monomer.

Figure 2A:
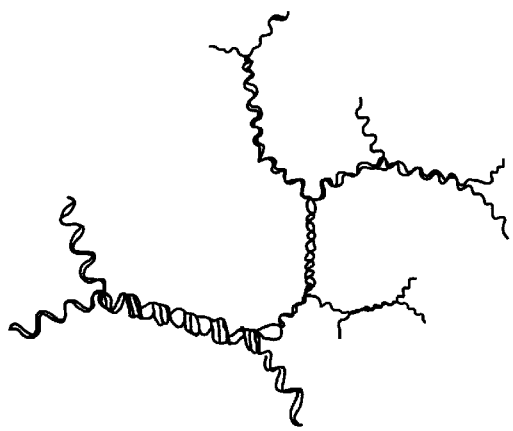
FIG. 2A schematically illustrates a 1-layer nucleic acid dendrimer, wherein an initiator monomer is hybridized to four B-type monomers.
Figure 2B:
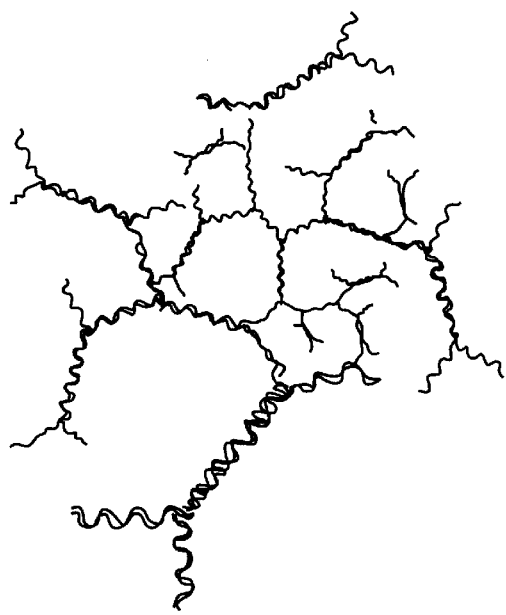
FIG. 2B schematically illustrates a 2-layer nucleic acid dendrimer.
Figure 2C:
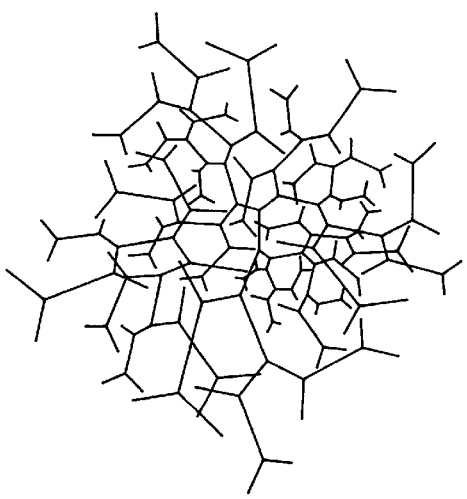
FIG. 2C schematically illustrates a 3-layer nucleic acid dendrimer.
Figure 2D:
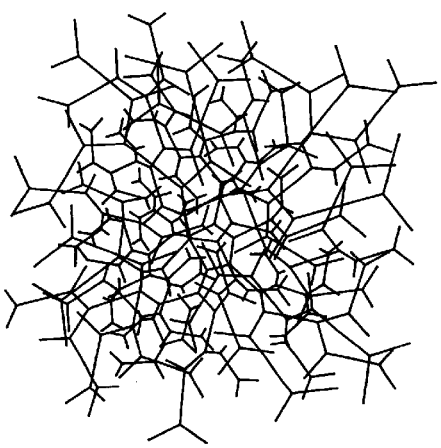
FIG. 2D schematically illustrates a 4-layer nucleic acid dendrimer. Note: The additional volume of the 3 and 4 layer dendrimers necessitates that they are represented proportionally smaller than the 1 and 2 layer dendrimers.

In a similar manner, strands numbered 6 and 7, hybridize with strand number 2, to form monomers C' and C". These C-type monomers have the ability to saturate by hybridization all of the single-stranded sites of monomers B' and B", thereby completing the assembly of the dendritic reagent through layer number 2, as illustrated in FIG. 2B. Alternating additions of B' and B" followed by C' and C" leads to dendrimer growth as depicted in FIGS. 2C and 2D.

Every monomer has four single stranded arms with one (–) arm for binding, so each addition triples the number of single stranded arms available for subsequent hybridization. The first layer has 12 arms, the second 36, the third 108, the fourth 324, etc. In addition to tripling the number of single stranded arms, the addition of each layer approximately doubles the total mass of the growing structure. 2-layer dendrimers have 17 monomers (initiating monomer, 4 monomers in the first layer, and 12 monomers in the second layer) and 36 ends and consequently, the third layer possesses 36 monomers. Thus, at every stage of dendrimer growth, two thirds of all the mass is in the surface layer.

The oligomers may have a wide variety of base composition and length. In preferred embodiments, the base composition is selected such that the oligomers have minimal non-specific homology and lengths that allow for specific hybridization but which are short enough for efficient production. The minimization of non-specific homology is significant in two respects. First, the reagents are extremely limited in their ability to self-hybridize. Second, they are limited in terms of the complementary portions of other reagents to which they hybridize and thus direct the assembly of the DNA matrices in a precise and controlled manner. In general, the lengths of the oligomers range from about 20 to about 200 bases.

In more preferred embodiments, the nucleic acid matrices of the present invention are prepared using "Euler"-type sequences. These matrices exhibit not only a lack of self-hybridization, but the Euler sequences hybridize only with their Euler complement. In these preferred embodiments, non-self hybridizing oligomers are prepared by designing a so-called master sequence characterized by the absence of repeated subsequences of a particular length. To calculate the length and composition of such a master sequence, the minimum length "X" of the non-repeated subsequence is selected so as to be as small as possible. The length (L) of the master sequence is then calculated using the following formula:

$$L=((4^x-P)\div 2)+(x-1)$$

wherein x=the length of the non-repeated subsequence; and P=number of palindromic subsequences having a length x. Palindromes exist only for subsequences having a minimum of 2 bases and an even number of bases. For example, when x=3 or 5, P=0.

Application of the formula to an embodiment in which x=2 (such that the master sequence contains no repeats of subsequences having 2 or more nucleotides) works as follows. First, the number of "2-mers" is calculated as $4^2=16$. The 16 2-mers are as follows: AA, AC, AG, AT, CA, CC, CG, CT, GA, GC, GG, GT, TA, TC, TG AND TT. There are 4 palindromes, namely: TA, AT, GC and CG. The design of the master sequence is started by choosing one of the 12 remaining 2-mers, which necessitates the choice of a second 2-mer complementary to the first 2-mer. The arbitrary selection of the 2-mer AA yields the following:

|    | 1 | 2 | 3 | 4 | 5 | 6 | 7 |
|----|---|---|---|---|---|---|---|
| 5' | A | A | — | — | — | — | — |
| 3' | T | T | — | — | — | — | — |

In this case, the selection of the 2-mer AA necessitates the selection of the 2-mer TT for the complementary strand. The selection of the third base for the top strand (i.e., the positive or Watson strand) must then be C or G, because the selection of A would violate the rule of having no repeats of 2-mers, and AT is a palindromic subsequence. Thus, choosing C results in the growing double-stranded master-sequence:

5' A A C 3'

3' T T G 5'

The 2-mers AC and GT are eliminated from further use. The next selection for the top strand may be A (i.e., CA), C (i.e., CC) or T (i.e., CT). The choice of "A" limits the fourth base to G (AG being the last 2-mer), whereas the choice of C or T allows for greater flexibility (i.e., A or T if C is chosen, and C or G if T were chosen). In designing the master sequence, the nucleotides should be chosen to maximize the choices for at least the next nucleotide. Choosing "C" results in the double-stranded sequence:

5' A A C C 3'

3' T T G G 5' such that the 2-mers CC and GG are eliminated as future choices.

The fifth base for the top strand may be A or T. The choice of A will dictate the sixth base to be G (as AG is now the last remaining 2-mer beginning with "A"). Choosing T on the other hand allows for C or G to be the sixth base. Thus, T is the choice for the fifth base of the top strand.

5' A A C C T 3'

3' T T G G A 5'

Now, CT and AG have been eliminated. Regardless of whether C or G is added as. the sixth base, A must be seventh base (because CA and GA are the last remaining available 2-mers from which to choose). The master sequence is then completed as follows:

5' A A C C T C A 3'

3' T T G G A G T 5' and all 12 2-mers have been utilized.

It is self-evident that many different master sequences that meet the same criteria can be designed. Plainly, the design of master sequences having no repeats of subsequences having lengths of 3, 4, or even 5 bases is more complicated than that of a master sequence having no repeats of subsequences having lengths of the two bases. Nonetheless, following the above rules readily leads to a master sequence. The present invention does not require that the entirety of the master sequence be characterized by having no repeats of subsequences having a single predetermined length. Portions of the master sequence may contain no repeats of subsequences having one predetermined length and other portions having no repeats of subsequences of a second, different length. Examples of such sequences, denoted as SEQ ID NOS:1 and 2, are set forth below. These two sequences both contain 261 base pairs, wherein the first 86 base pairs have no repeats of subsequences having a length of greater than 3 bases, and the entire sequence, i.e., bases 1–261, has no repeats of subsequences having lengths greater than 4 bases.

>CGACAAAAGA ACTGAGGAAG TGGGGTAATG ATAGAG-
CAAC AGGTGACGGA TGGCAGACTA AATACACGAA
ACCAAGGGAG ATTGAATTAA GCTAGGCTGG ACCGAG-
TAGA AAAATGTGCA TAACGTACAA TATAAAGTAA
GATCGAATCA AACATGAAGG ATACGCAAGC GAT-
GCTAACT ATGGAACGAG AGGTAGGGCG GGACA-
GAAGA CGCCCAGTGA GTCGGCCAAC CGGAGCGGCA
CGGGTGTGGT CAGGCGAACA A (SEQ ID NO:1)

>TTGTTCGCCT GACCACACCC GTGCCGCTCC GGTTGGC-
CGA CTCACTGCGC GTCTTCTGTC CCGCCCTACC
TCTCGTTCCA TAGTTAGCAT CGCTTGCGTA TCCT-
TCATGT TTGATTCGAT CTTACTTTAT ATTGTACGTT
ATGCACATTT TTCTACTCGG TCCAGCCTAG CTTAAT-
TCAA TCTCCCTTGG TTTCGTGTAT TTAGTCTGCC ATC-
CGTCACC TGTTGCTCTA TCATTACCCC ACTTCCTCAG
TTCTTTTGTC G (SEQ ID NO:2)

Figure 3:
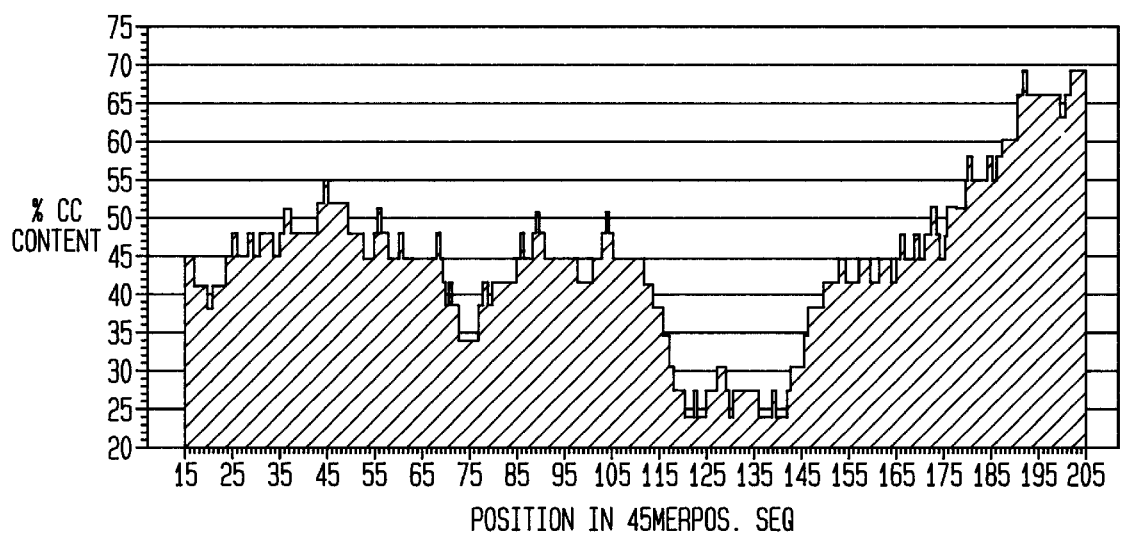
FIGS. 3 and 4 are bar graphs showing the GC content for oligomeric subsequences having lengths of 29 and 49 bases, respectively, obtained from a preferred master DNA sequence above.
Figure 4:
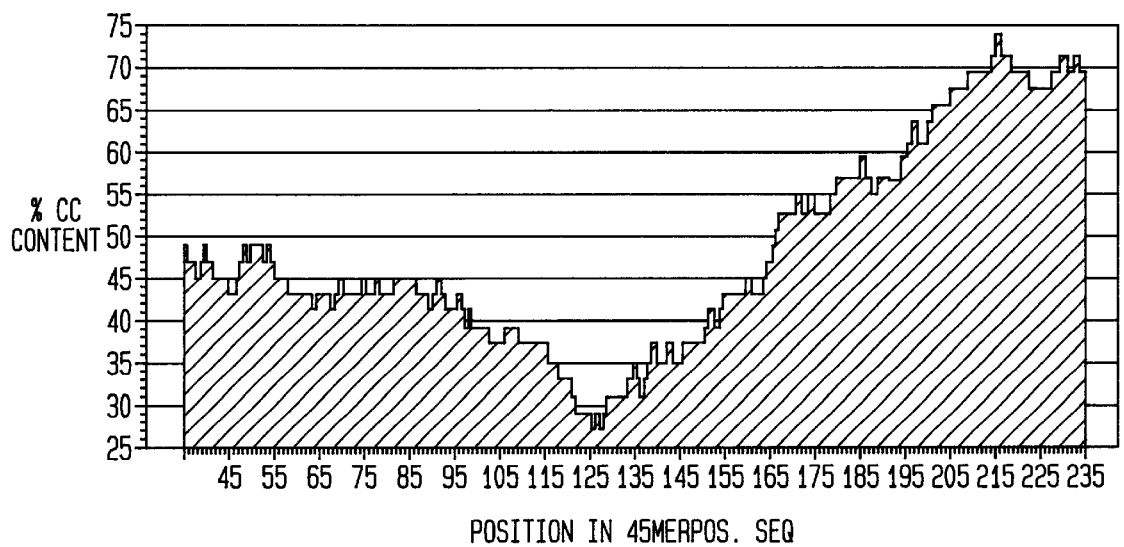

Depending upon the desired result, different portions of these master sequences may be chosen as the oligomers that ultimately constitute the waist or arm sequences of the monomers. For example, selection of a sequence of a given length with a relatively high GC content will result in a oligomer having a relatively high melting temperature. This is advantageous in designing structures that will partially melt, i.e., denature, in a controlled and predictable manner. FIGS. 3 and 4 are bar graphs showing the GC content for subsequences having lengths of 29 and 49 bases, respectively, for the master sequences above. The partial sequence defined by the first 86 bases in the sequence analyzed in FIG. 8 have no repeats greater than 3 bases, and the sequence defined by bases 1–261 have no repeats greater than 4 bases. The same is true for the respective partial sequences analyzed in FIG. 9. This type of analysis would enable one skilled in the art to select a portion of the master sequence having a predetermined melting point. Master sequences may also be chosen so as to maximize the flexibility in the selection of the various waist and arm sequences. For example, 4 30-base arm oligomers and 2 50-base waist oligomers, each having different melting points, etc., are more easily chosen from a master sequence containing greater than 220 (i.e., (4×30)+(2×50)) bases in length as opposed to a master sequence having a length of exactly 220 bases.

In a more preferred embodiment, the master sequence contains no repeats of subsequences having 4 or more nucleotides. In these embodiments, the master sequences will have a length (L) of $((4^4-16)\div 2)+(4-1)=123$ bases, double-stranded. The sixteen palindromic sequences (i.e., P=16) are as follows: AATT, TTAA, CCGG, GGCC, TATA, ATAT, GCGC, CGCG, ACGT, TCGA, AGCT, TGCA, CATG, CTAG, GATC and GTAC. Dividing the 123 bases evenly amongst the a, b, c, d, & e monomers yields 24 bases for each monomer (i.e., 24-mers). 24-mers have a relatively low melting temperature (–55–70 C.), so in preferred embodiments, the master sequence used in the matrix assembly contains no repeats greater than 4 bases for >30 base a, b, c, d, and e sequences. In these embodiments, master double stranded sequences 516 bases long may be assembled (i.e., $(4^5\div 2)+(5-1)=516$). Oligonucleotides ranging in size from 30 to 100 bases with no repeats greater than four bases are constructed based on a master sequence having 512 bases.

The use of the Euler sequences results in oligomers which allow for extremely precise and controlled assembly of the nucleic acid matrices of the invention. The oligomers and the monomers that are assembled therefrom have negligible or no capability of self-hybridization. That is, they hybridize only to the oligomer or monomer having a complementary euler sequence, and thus reduce interference with the assay. The result is greater accuracy and sensitivity. For example, two single-stranded oligomers containing multiple, non-repeated 3-mers obtained from the same or different master sequences containing no repeats of subsequences having three or more bases, will have a minimum 33% mismatch in base pairing. Similarly, any two single-stranded oligomers having multiple non-repeated 4-mers designed from the same or different master sequences having no repeats of subsequences having four or more bases will have a minimum 25% mismatch. In the case of oligomers having multiple, non-repeated 5-mers, the minimum mismatch will be 20%. This degree of sequence dissimilarity between oligomeric waist and arm sequences further ensures that each waist and arm will bind only to its Euler complement. These embodiments are equally applicable to the design of matrices containing isoc nucleic acid, isoT nucleic acid and inosine-containing nucleic acid, because they are all governed by the hybridization rules for DNA.

Figures 5, 7:
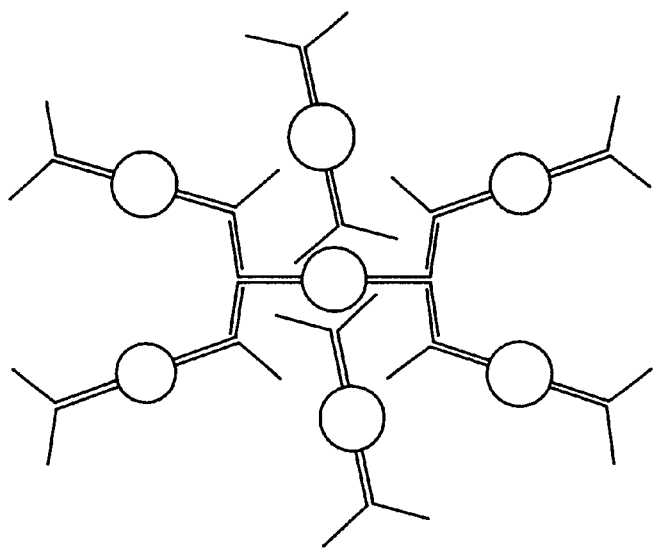
FIG. 5 is a schematic diagram of a "bubble-waist" monomer structure.
FIG. 7 illustrates four-strand nucleic acid dendritic configurations.

The monomers for preparation of the dendrimers of the present invention possess an intermediate region containing a double-stranded waist and two single-stranded arms at each end. In other embodiments, monomers wherein one end of the monomer has only one single-stranded arm, are employed. In yet other embodiments, both types of monomers are employed. Monomer reagents with three single stranded regions may, in some instances, be pref erred, because they provide less steric hindrance and larger liquid volumes in the dendrimer interior. Also, as illustrated in FIG. 5, the intermediate region portion of the monomer need not be fully double-stranded along its entire length, but may include single-stranded portions intermediate of the monomer ends. Such monomer structures possess a greater number of hybridization sites, should that be desired.

Dendritic assembly via hybridization may begin with an initiator nucleic acid molecule having three or more single stranded regions. In these cases, hybridization of nucleic acid molecules to the free single stranded ends of the initiator generates the first layer product. In the case of hybridization of an initiator with three arms with three-armed dendrimer monomers, a first layer having six arms is produced.

The more preferred seven strand dendritic structure utilizes monomers with four arms; consequently, the first layer possesses twelve arms. Subsequent layers of hybridization lead to a geometric expansion of the single-stranded ends and a three-dimensional dendritic organization of nucleic acids.

Dendrimer assembly proceeds from purified single-stranded nucleic acid molecules to annealing of the dendrimer monomers, followed by the assembly of an ordered nucleic acid structure in solution or on a solid support. As used in this context, the "nucleic acid dendrimers" are complexes of nucleic acid comprising subunits of partially double-stranded nucleic acid molecules.

Figure 6:
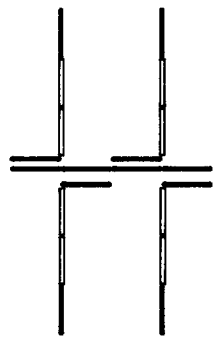
FIG. 6 illustrates two-strand nucleic acid dendritic configurations.
Figure 6:
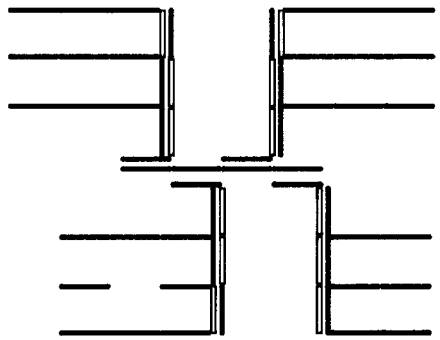

As illustrated in FIG. 6, a nucleic acid dendrimer of the present invention may be assembled from as few as two single stranded nucleic acids where strand 1=[seq1(+)]$_n$[seq2(–)], strand 2=[seq2(+)]$_n$[seq1(–)], and seq1 and seq2 are nucleic acid sequences and (+) and (–) designate complementary sequences (see FIG. 6). Sequential hybridization of excess strand 2 to strand 1 followed by alternating excess strand 1 and strand 2 yields a dendritic structure, given that n is two or greater. One would expect the structure produced by two single strands to be inhomogeneous, since any stoichiometry of strand 1 with strand 2 could semi-randomly polymerize by hybridization.

The addition of a third strand containing only (+) sequence elements may be used as an initiator, thereby reducing the inhomogeneity of the growing structures. In effect, three types of dendritic monomers (the single stranded nucleic acids) are needed for controlled polymerization by hybridization, an "A" monomer which is the initiator and which carries only (+) sequences, a "B" monomer which forms the first layer which contains a single (−) sequence complementary to a sequence on the "A" monomer and multiple (+) sequences which differ from the (+) sequences found on the "A" monomer, and a "C" monomer which contains a single (−) sequence complementary to the (+) sequence from the "B" monomer and multiple (+) sequences identical to the (+) sequences of the "A" monomer.

A further modification of the dendrimer assembly, illustrated in FIG. 7, utilizes four strands, wherein strand 1=[seq1 (+)]$_n$, strand 2=[seq1(−)][seq2(+)]$_n$, strand 3=[seq2(−)][seq3 (+)]$_{n'}$, and strand 4=[seq3(−)][seq1(+)]$_{n'}$. These dendrimers are composed of initiator "A" monomer, first layer "B" monomers, second layer "C" type monomers and third layer "D" type monomers, followed by sequential addition of B, C and D type monomers. Dendritic structures can be made even more complex with increasing types of monomers. However, minimizing the number of reagents is preferred.

Figure 8:
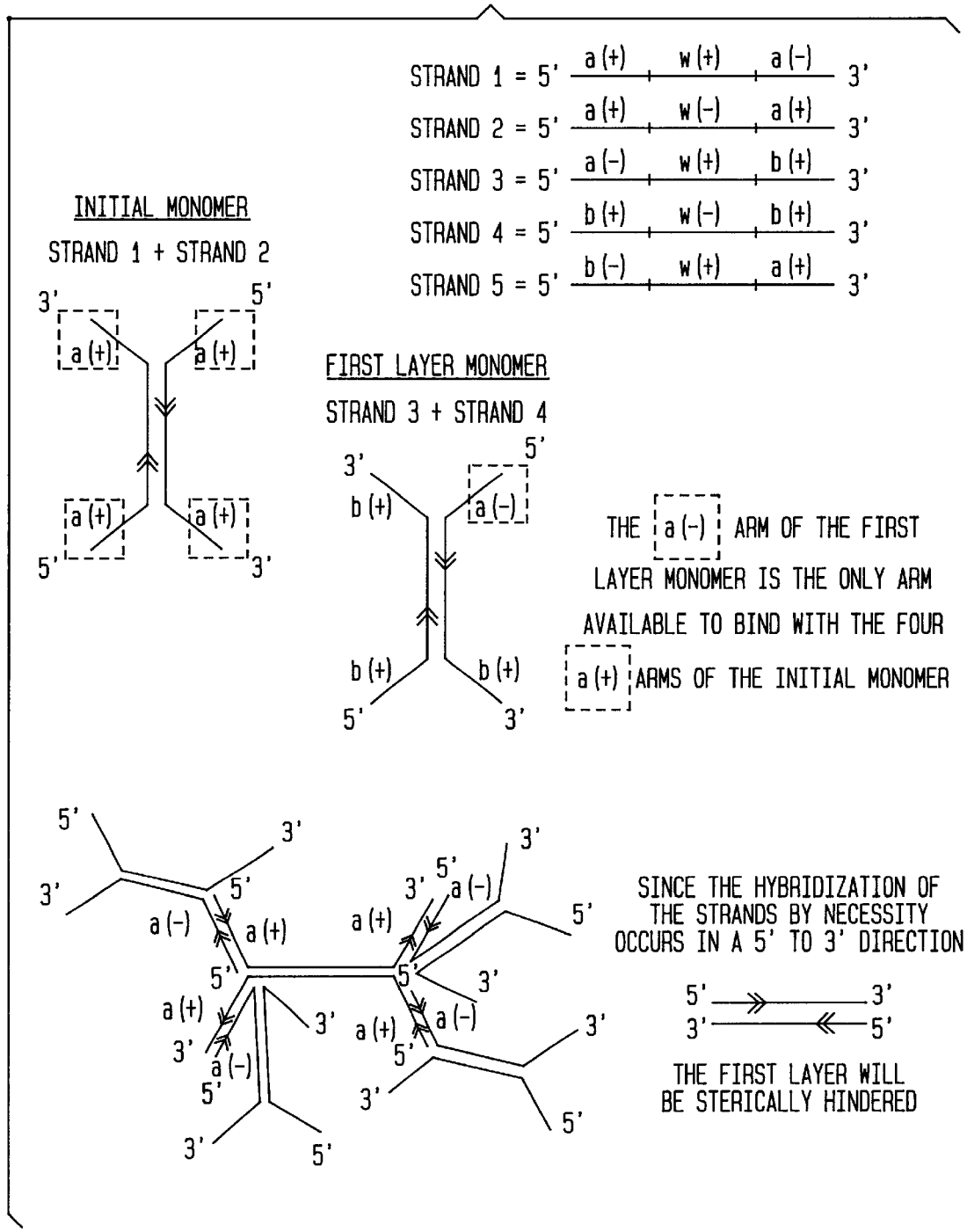
FIG. 8 is an illustration of the steric constraints created by utilizing 5 strands for the assembly of dendrimers utilizing four-arm dendrimer monomers. The structures are "nucleic acid trees" or dendrimers composed of layers of nucleic acid, each layer being composed of partially single-stranded heteroduplex, herein referred to as dendrimer monomers. The outermost layer of a given nucleic acid dendrimer would have multiple single-stranded arms capable of hybridization with a complimentary nucleic acid sequence. Dendrimer monomers have the property that sequential addition of monomers would yield a three-dimensional structure composed of nucleic acid.
Figure 9:
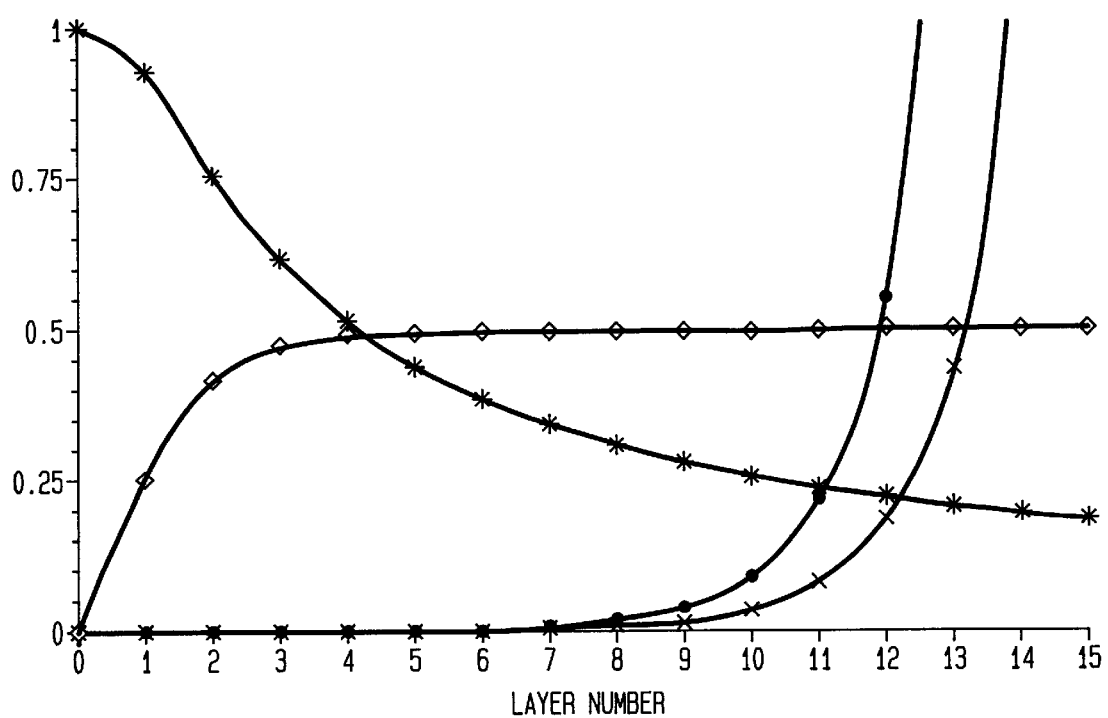
FIG. 9 is a graph illustrating nucleic acid dendritic growth, wherein (*) represents the ratio of shell volume to sphere volume, (♦) represents the ratio of total volume of the dendrimer through the k−1 layer to volume added by layer k, (X) represents the ratio of total volume dendritic DNA through layer k to sphere volume k, and (●) represents the ratio of volume of dendritic DNA added in layer k to shell volume of layer k.

Three single strands could serve as the three monomers. However, the resulting comb-like structure would likely be sterically hindered within a few cycles of hybridization. Partially double-stranded monomers consisting of two single strands of nucleic acid can overcome the steric hindrance of the comb-like structure. In this configuration, each single stranded molecule has three regions, 5'→3+= [arm1seq][waistseq][arm2seq]. In this configuration, each dendrimer monomer consists of two single stranded nucleic acid molecules, yielding molecules with four single stranded arms and a double stranded waist region. Assembly of the initiator-A, first layer-B and second layer-C monomers can be accomplished with as few as five single stranded nucleic acid molecules. As shown in FIG. 8, however, the resulting structure would have increased steric hindrance resulting from the necessary constraint of having two of the waists of the monomers on the same end of two of the arm sequences of each monomer.

Maximal spacing of the dendrimer monomers can be accomplished with as few as seven single-stranded nucleic acids. Another refinement is the incorporation of two different waist sequences, which serves to minimize strand exchange between dendrimer monomers and further limits undesirable hybridization events. In addition, the resulting dendrimers display two types of single stranded arms in equal quantities at each layer, thereby allowing one type of arm to be used for hybridization to a particular target sequence and the other arm to be used for attachment of signal molecules.

To reinforce and help maintain the structural integrity of the assembled nucleic acid dendrimer, a plurality, and preferably all of the inter-monomer linkages (i.e., the complementary arms that are hybridization bonded) are cross-linked. In more preferred embodiments, the double stranded waist region of a plurality of, or even more preferably, all monomers is also cross-linked. Applicant has discovered that cross-linking the matrix at these locations results in a substantially more stable structure. Cross-linking may be conducted with a variety of agents, in accordance with standard procedures. Suitable cross-linking agents include mitomycin C (e.g., Tomasz, et al., Science 235:1204–1208 (1987); Basu et al., Biochemistry 32:4708–4718 (1993); Borowy-Borowski et al., Biochemistry 29:2999–3006 (1990); and Norman et al., Biochemistry 29:2861–2895 (1990)), daunomycin and other anti-cancer agents that exert an anti-cancer effect by cross-linking DNA, ethidium diazide, Cisplatin, EDC-type compounds and psoralens.

Those skilled in the art will recognize that the sequence requirements and the operating conditions vary depending on the specific cross-linking agent. See, e.g., in addition to the aforementioned publications, Summerton et al., J. Mol. Biol. 122:145–162 (1978). For example, mitomycin C prefers 5' CpG. As for reaction conditions in general, cross-linking reactions are carried out at Tm of about −20° C., and neutral pH. Ample guidance is provided in the literature to enable one skilled in the art to cross-link the nucleic acid dendrimers of the present invention. See, e.g., The Pierce Catalog, and U.S. Pat. No. 5,543,507, entitled "Covalently Cross-linked Oligonucleotides," and the literature reviewed therein, specifically Grineva et al., FEBS., 351–355 (1973); Summerton et al., J. Mol. Biol. 122:145–162 (1978); Summerton et al., J. Theor. Biol. 78:61–75 (1979); U.S. Pat. No. 4,123,610; Meyer et al., J. Amer. Chem. Soc., 111:8517–19 (1989); Matteucci et al., Nucleic Acids Res., 14:7661–7674 (1986); Matteucci et al., Tetrahedron Letters, 28:2469–2472 (1987); Ferentz, et al., J. Am.Chem. Soc., 113:4000–4002 (1991); Lee, et al., Biochemistry, 27:3197–3203 (1988); Manoharan, et al., J. Am. Chem. Soc., 109:7217–7219 (1987); Manoharan, et al., J. Am. Chem. Soc., 110:2690–2691 (1988); Vasseur, et al., Nucleosides & Nuclotides 8:863–866 (1989); Bertrand, et al., Nucleic Acids Research, 17:10307–10319 (1989); Philippe, et al., Tetrahedron Letters, 31:6347–6350 (1990); P. Iyer, et al., Nucleic Acids Research, 18:2855–2859 (1990); Groehke, et al., Helvetica Chimica Acta, 73:608–617 (1990); and Peoc'h et al., Tetrahedron Letters, 32:207–210 (1991).

Psoralen treatment is preferred. Because of their planar structure, psoralens can intercalate between the base parts in the double helical molecular structure of the nucleic acids. Upon radiation with light of the proper UVA wavelength, e.g., from about 315 nm to about 350 nm, the psoralens may form covalent bonds with pyrimidine nucleotides that occur as integral entities of nucleic acid strands. In addition to psoralen, psoralen derivatives suitable for cross-linking include 8-methoxy psoralen, 4,5',8-trimethylpsoralen, and 4'-adducts of trioxsalen (e.g., 4'-hydroxymethyl-4,5',8-trimethyl psoralen, 4'-methoxymethyl-4,5',8-trimethyl psoralen, 4'N-Phthalimidomethyl-4,5',8-trimethyl psoralen, and 4'-aminomethyl-4,5',8-trimethyl psoralen ydrochloride). See, e.g., U.S. Pat. No. 4,196,281.

In general, cross-linking by psoralens is conducted according to standard procedures. See, e.g., Cimino et al., Annu. Rev. Biochem. 54:1151–1193 (1985); Shi et al., Biochemistry 25:5895–5902 (1986); and Cimino et al., Biochemistry 25:3013–3020 (1986). See also U.S. Pat. No. 4,196,281, entitled "PSORALENS", directed to the trioxsalen 4'-adducts as nucleic acid cross-linking agents. The '281 patent provides further guidance on the determination of various reaction parameters such as the solubility of the psoralen in aqueous solution, and the dissociation constant for the non-covalent binding of the psoralen to nucleic acid. Thus, the higher the solubility, the greater number of molecules in the surrounding liquid medium available to binding sites. Similarly, the lower the dissociation constant, the greater the number of psoralens occupying a potential binding site at any moment in time. In preferred embodiments, the Tm is about −20° C., the concentration of nucleic acid is less than about 100 ng/jil, and the psoralen is recrystallized immediately prior to use.

The polyanionic nature of nucleic acids insures that nucleic acid constructs are nearly spherical, liquid within, and have different concentrations of nucleic acid in different layers. With each successive addition, the volume of the theoretical sphere capable of containing a particular layer increases by the additional volume present in the last layer of hybridization, i.e., the shell layer. Also, the nucleic acid added with each layer increases very rapidly and approaches twice the sum of all the nucleic acid present before the addition. Thus, as additional layers accumulate, the partial volume of the sphere contributed by the shell diminishes while the partial volume of the nucleic acid present in the nucleic acid dendrimer doubles. Obviously, the volume of nucleic acid present in the shell or last addition layer cannot be greater than the volume of that shell— a saturation of the shell occurs at some layer number. The layer in which the saturation of nucleic acid in the shell occurs defines the beginning of a semipermeable nucleic acid membrane, and is indicated experimentally by a nearly linear progression of total nucleic acid comprising the dendrimer, as opposed to the geometric progression of total nucleic acid observed prior to saturation. The saturation of nucleic acid in the shell could be due to steric (volume/volume) hindrance, or the high concentration of negative charge in the shell. In either case, additional nucleic acid is partially excluded from forming all possible hybrids even in the shell layer, and completely excluded from the interior of the dendrimer.

Dendrimers constructed from monomers of the same or similar configuration may be described in terms of the following parameters: the total number of monomers, the number of monomers added in a given addition layer, the sphere radius, the sphere volume, the shell volume, the nucleic acid (NA) total volume and the nucleic acid volume added in a given addition cycle. For dendrimers constructed with varying geometries and sizes of the monomer, adjustments must be made in the description of the monomer at each addition number. However, even monomers of various structures, weighted average values for total bases, length in bases, volume, mass, hybridization sites and hybridization site length may be used in a description to approximate non-uniform nucleic acid dendrimers. A model of uniform nucleic acid dendrimers follows.

A nucleic acid (NA) dendrimer is defined as a collection of at least three single stranded nucleic acid molecules held in close association via intermolecular base pairing, optionally reinforced by intermolecular covalent crosslinks. A dendrimer monomer is defined as a single or group of NA strands used in the assembly of a NA dendrimer. This model uses four dendrimer monomer variables:

m=monomer total bases
n=monomer length in bases
j=monomer hybridization sites and,
p=hybridization site length in bases.

These variables are sufficient to model NA dendritic growth.

The dendrimer monomer length is derived from n and is defined as the average longest dimension projected radially from the initiating dendrimer monomer as measured in solution. Dendrimer monomer length is approximated by the number of bases in the longest single strand of a monomer times the distance per base.

Dendrimer monomer length in nm=n bases*0.34 nm/base=q nm

Another important length used in the model is the hybridization site length,

Monomer hybridization site length in nm=p bases*0.34 nm/base=r nm

The volume of a dendrimer monomer is defined as the total solvent displaced by a single monomer. The dendrimer monomer volume is approximated by treating the monomer as a cylinder with diameter 1.0 (nm) and length as defined above.

Dendrimer monomer volume in $nm^3 = p*(1\ nm)^2*q\ nm = s\ nm^3$

The mathematical model of nucleic acid dendritic assembly makes several assumptions. The first assumption is that the dendrimer monomers contribute full length minus the hybridization site length to theoretical sphere radius. Secondly, the model assumes that for each addition the added monomers are located in the shell layer. Finally, the effects of pH, temperature and salt concentration are assumed to be negligible.

Zeroth (Initiating) Layer of a Nucleic Acid Dendrimer

A single monomer is defined as layer number zero.

$k=0$

Sphere Volume $(0) = (4/3)*p*(radius)^3$

Radius (0) for the zeroth layer is one half monomer length.

i.e. Sphere Volume $(0) = (4/3)*p*(q\ nm/2)^3$

Shell Volume (0) for layer number zero equals sphere volume for the zeroth layer.

NA Total Volume (0) for layer number zero equals the volume of one monomer.

i.e. NATotal Volume $(0) = s\ nm^3$

NA Volume Added (0) for layer number zero equals NA Total Volume (0).

First Layer of a Nucleic Acid Dendrimer $k=1$

In general, the monomers added at layer number one are equal to the number of hybridization sites available per initiating monomer.

Radius $(1) = q/2 + q - r$

Sphere Volume $(1) = (4/3)*p*(q/2+g-r)^3$

Shell Volume $(1) =$ Sphere Volume $(1) - s$

NA Volume $(1) = j*s$

NA Volume Total $(1) = (1+j)*s$ $k^{th}$ Layer for Generalized Dendrimer (k>0)

$$\text{Monomers Total } (k) = 1 + \frac{j*(1-(j-1)^k)}{2-j}$$

Monomers Added $(k) = j*(j-1)^{(k-1)}$

Sphere Radius $(k) = q/2 + k*(q-r)$

Sphere Volume $(k) = (4/3)*p*(q/2+k*(q-r))^3$

Shell Volume $(k) = $ (Sphere Volume $(k)$) − (Sphere Volume $(k-1)$)

NA Volume Total $(k) = $ (Monomers Total $(k))*s$

NA Volume Added $(k) = $ (Monomers Added $(k))*s$

Successive additions of nucleic acid would result in the eventual saturation of the sphere surface, thereby leading to the "membrane character" of the reagents; the potential nucleic acid volume added would be greater than the increase in the volume of the sphere available. Following layer 11, the nucleic acid would occupy ~90% of all available surface volume, representing an approximate density of over 899 mg/ml. The concentration of nucleic acid at the surface of the dendrimer would be extremely high, and the majority of all nucleic acid molecules would be free near the surface for hybridization to complementary sequences. Furthermore, the high concentration of nucleic acid on a sphere of more than 10 cycles (though fewer cycles may have the desired semipermeable properties) may obviate non-specific absorption of nucleic acid into the spherical dendritic structure.

The predicted parameters of a dendritic nucleic acid produced for up to 20 successive monomer additions are shown in Table 1, which is a mathematical treatment of our construct of monomers formed into nucleic acid dendrimers. At the higher layer numbers the model is clearly beyond the saturation of nucleic acid in the shell or surface layers. FIG. 3 is a graphical representation of the volume relationships as a function of addition number.

The assembly of the nucleic acid dendrimer monomers into nucleic acid dendrimers could be conducted on a solid support, i.e., a water-insoluble substrate such as fluorescent polystyrene balls, nylon membranes, nitrocellulose and the like. The core dendrimer monomer "A" would be replaced by a starter layer of single-stranded nucleic acid fixed to the solid surface. The starters layer of nucleic acid selected could be complementary to any of the single-stranded arms of the B', B", C', C" monomers described above. Sequential hybridization with excess (B'+B") followed by a washing step (rinsing a membrane support or centrifugation of polystyrene balls) followed by hybridization with an excess of (C'+C"), etc., would lead to a semipermeable nucleic acid surface affixed to a solid support.

Predicted Hybridization Kinetics of Nucleic Acid Dendrimers

Again, without intending to be bound by any particular theory of operation, the amount of DNA needed in the dendrimers to arrive at a reasonable reaction rate for hybridization can be calculated. The rate of renaturation of completely denatured DNA is kinetically a second-order reaction, and the renaturation rate constants for DNA's are given approximately by:

$$k_2 = \frac{3e+5 \times L^{0.5}}{N} \text{ Liters mole}^{-1} \text{ sec}^{-1}$$

where L=length of shortest single strand, and N=complexity of DNA, or the number of non-repetitive base pairs (Wetmur & Davidson, J. Mol. Biol. 31:349–370 (1968). The predicted rate of annealing of nucleic acids should apply to dendritic molecules since the experimental values of $k_2$ have been shown applicable to sheared and unsheared bacteriophage T4 and T7, and *E. coli* DNAs, which have comparable molecular weight to the predicted mass of the nucleic acid dendrimers.

As an example, a six layer dendrimer constructed from 110-base monomers would be composed of 1,457 monomers, corresponding to a total of 160,270 basepairs. This size contrasts with 39,936 basepairs of T7 bacteriophage DNA; i.e. the 6-layer dendrimers are about 4× larger than T7 DNA. These dendrimers have 2,916 single-stranded arm sequences, 1,458 arms of two types, available for hybridization to a single 50 nucleotide (nt) long sequence DNA to be detected.

Because each reaction leads to the same 50 base pairs, N=50. L is the length of the shortest single-stranded region participating in the reaction, in this case L=50. Thus, the rate constant is:

$$k_2 = \frac{3e5 * 50^{0.5}}{50} = 4.24\,e+4 \text{ L mole}^{-1} \text{ sec}^{-1}$$

One assumes that the reaction is driven by the DNA matrix concentration (in order to mimic sensitive detection conditions). One can ignore the concentration of the target DNA in the sample, and thus determine the concentration of dendrimer DNA needed to effect the desired annealing parameters. If the concentration of dendrimer is 1 mg/ml, i.e. 3e-6 M, and since 50% of the nucleotides are available for reaction, i.e. one-half of the ss arms:

$C_0$ of single stranded arms=3e-6/2=1.5e-6 molar.

Thus the half reaction time, $t_{1/2}$=ln2/[4.24e4*1.5e-6]=11 seconds or $t_{3/4}$<0.5 min. This calculation has been verified to predict accurately the results of annealing of oligonucleotides to complementary sequences covalently tethered to the surface of beads. This calculation assumes that all of the dendrimer oligonucleotides are available for reaction (or the rate is proportionally decreased) and that mixing is complete (or the reaction consists of a fast homogeneous reaction followed by a slower diffusion-controlled reaction). For the example given, i.e. dendrimer concentration equal to 1 mg/ml, more than 75% of all possible bridges will be formed in thirty seconds. Note, 1 mg/ml equals 1 ng/ml so a 50 ml reaction would require only 50 ng of DNA dendrimer for 75% capture of a 50 mer nucleic acid molecule, independent of the concentration of the 50 mer.

TABLE 1

| Matrix Monomer Bases Total | 220 |
|---|---|
| Matrix Monomer Length Bases | 110 |
| Matrix Monomer Length (nm) | 37.4 |
| Matrix Monomer Volume (nm)^3 | 2.94e + 01 |
| Matrix Monomer Mass (mg) | 1.21e – 16 |
| Monomer Hybridization Sites | 4 |
| Hybridization Site Length (BP) | 30 |
| Hybridization Site Length (nm) | 10.2 |

| Addition # | Total Monomers | Monomers Added | [Total DNA] mg/ml | [Shell DNA] mg/ml |
|---|---|---|---|---|
| 0 | 1 | 1 | 4 | 4 |
| 1 | 5 | 4 | 1 | 1 |
| 2 | 17 | 12 | 1 | 1 |
| 3 | 53 | 36 | 2 | 2 |
| 4 | 161 | 108 | 2 | 3 |
| 5 | 485 | 324 | 4 | 6 |
| 6 | 1,457 | 972 | 7 | 12 |
| 7 | 4,373 | 2,916 | 14 | 27 |
| 8 | 13,121 | 8,748 | 29 | 62 |
| 9 | 39,365 | 26,244 | 62 | 148 |
| 10 | 118,097 | 78,732 | 138 | 361 |
| 11* | 254,293 | 236,196 | 317 | 899* |
| 12* | 1.06e + 0.6 | 708,588 | 744* | 2,273* |
| 13* | 3.193 + 0.6 | 2.13e + 0.6 | 1,778* | 5,824* |
| 14* | 9.57e + 0.6 | 6.38e + 0.6 | 4,317* | 15,096* |

*For these layer numbers the concentration of nucleic acid is predicted to be at or above a saturated solution, i.e. the model has broken down and the number of single stranded arms, the mass and predicted concentration of DNA must all have lower values.

ABBREVIATIONS

BP=basepair
$c_0$=concentration at zero time
DNA=Deoxyribonucleic Acid
ds=double-stranded l=liters
ln=natural logarithm
M=Molar
-mer=oligomer
mg=milligram
ml=milliliter
NA=nucleic acid
nm=nanometers
nt=nucleotide
RNA Ribonucleic Acid
ss=single-stranded
t=time
mg=microgram
ml=microliter

SYMBOLS

*=multiplication
p=pi~3.1415926
^=raised to the power e=base 10 exponent
[ ]=concentration
The dendritic polynucleotides of the present invention may be used to prepare compositions as claimed in U.S. Pat. No. 5,175,270 and in assays as disclosed and claimed in U.S. Pat. No. 5,487,973.

All patent and non-patent publications cited in this specification are indicative of the level of skill of those skilled in the art to which this invention pertains. All these publications and patent applications are herein incorporated by reference to the same extent as if each individual publication or patent application was specifically and individually indicated to be incorporated by reference.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A polynucleotide matrix having a plurality of single stranded hybridization arms; said polynucleotide matrix comprising a plurality of polynucleotide monomers bonded together by hybridization; each polynucleotide monomer having an intermediate region comprising a linear, double stranded waist region having a first end and a second end, said first end terminating with two single stranded hybridization regions, each from one strand of the waist region, and said second end terminating with one or two single stranded hybridization regions, each from one strand of the waist region; and in said polynucleotide matrix each polynucleotide monomer is hybridization bonded to at least one other polynucleotide monomer at at least one such hybridization region;

and wherein each of said hybridization regions and said waist regions of said plurality of monomers comprise sequences obtained from a master sequence containing no repeats of subsequences having X nucleotides, wherein X represents an integer of from 2 to 6.

2. The polynucleotide matrix of claim 1, wherein the plurality of matrix polynucleotide monomers present does not exceed saturation of the dendritic polynucleotide.

3. The polynucleotide matrix of claim 1, wherein hybridization regions that are bonded together are cross-linked.

4. The polynucleotide matrix of claim 1, wherein waist regions of said monomers are cross-linked.

5. The polynucleotide matrix of claim 1, wherein waist and hybridization regions are cross-linked.

6. A composition for use as a hybridization reagent for detection of a nucleic acid sequence, comprising a polynucleotide matrix having a plurality of single stranded hybridization arms; said polynucleotide matrix comprising a plurality of polynucleotide monomers bonded together by hybridization; each polynucleotide monomer having an intermediate region comprising a linear, double stranded waist region having a first end and a second end, said first end terminating with two single stranded hybridization regions, each from one strand of the waist region, and said second end terminating with one or two single stranded hybridization regions, each from one strand of the waist region; and in said polynucleotide matrix each polynucleotide monomer is hybridization bonded to at least one other polynucleotide monomer at at least one such hybridization region;

and wherein each of said hybridization regions and said waist regions of said plurality of monomers comprise sequences obtained from a master sequence containing no repeats of subsequences having X nucleotides, wherein X represents an integer of from 2 to 6.

7. The polynucleotide matrix of claim 1, wherein X is 3.
8. The polynucleotide matrix of claim 1, wherein X is 4.
9. The polynucleotide matrix of claim 1, wherein X is 5.

10. A polynucleotide monomer comprising an intermediate region comprising a linear, double stranded waist region having a first end and a second end, said first end terminating with two single stranded hybridization regions, each from one strand of the waist region, and said second end terminating with one or two single stranded hybridization regions, each from one strand of the waist region; and wherein each of said hybridization regions and said waist region of said monomer comprise sequences obtained from a master sequence containing no repeats of subsequences having X nucleotides wherein X represents an integer of from 2 to 6.

11. The polynucleotide monomer of claim 10, wherein said second end terminates with one single stranded hybridization region.

12. The polynucleotide monomer of claim 10, wherein said second end terminates with two single stranded hybridization regions.

* * * * *

UNITED STATES PATENT AND TRADEMARK OFFICE
CERTIFICATE OF CORRECTION

PATENT NO.    : 6,274,723 B1
DATED         : August 14, 2001
INVENTOR(S)   : Thor Nilsen It is certified that error appears in the above-identified patent and that said Letters Patent is hereby corrected as shown below:

Column 1,
Line 9, cancel "the".

Column 4,
Line 9, "Ireagents," should read -- reagents, --.

Column 5,
Line 66, insert "3" on a separate line after "5' A A --".
Line 68, insert "5" on a separate line after "3'TT --".

Column 7,
Line 54, "-55-" should read -- ˉ55- --.

Column 8,
Line 17, "isoc" should read -- isoC --.
Line 27, "pref erred" should read -- preferred --.

Column 9,
Line 19, "$_n$." should read -- $_{n..}$ --.
Line 32, "3+" should read -- 3' --.

Column 13,
Line 60, "with-39,936" should read -- with 39,936 --.

UNITED STATES PATENT AND TRADEMARK OFFICE
CERTIFICATE OF CORRECTION

PATENT NO. : 6,274,723 B1
DATED : August 14, 2001
INVENTOR(S) : Thor Nilsen

It is certified that error appears in the above-identified patent and that said Letters Patent is hereby corrected as shown below:

Column 14,
Line 53, "254,293" should read -- 354,293 --.

Column 15,
Line 11, "RNA Ribonucleic Acid" should read -- RNA=Ribonucleic Acid --.

Signed and Sealed this

Twenty-sixth Day of February, 2002

Attest:

JAMES E. ROGAN
*Attesting Officer*  *Director of the United States Patent and Trademark Office*

SEQUENCE LISTING

<160> NUMBER OF SEQ ID NOS: 2

<210> SEQ ID NO 1
<211> LENGTH: 261
<212> TYPE: DNA
<213> ORGANISM: Unknown Organism
<220> FEATURE:
<223> OTHER INFORMATION: Description of Unknown Organism: illustrative
      DNA sequence

<400> SEQUENCE: 1
cgacaaaaga actgaggaag tggggtaatg atagagcaac aggtgacgga tggcagacta        60
aatacacgaa accaagggag attgaattaa gctaggctgg accgagtaga aaaatgtgca       120
taacgtacaa tataaagtaa gatcgaatca aacatgaagg atacgcaagc gatgctaact       180
atggaacgag aggtagggcg ggacagaaga cgcgcagtga gtcggccaac cggagcggca       240
cgggtgtggt caggcgaaca a                                                 261

<210> SEQ ID NO 2
<211> LENGTH: 261
<212> TYPE: DNA
<213> ORGANISM: Unknown Organism
<220> FEATURE:
<223> OTHER INFORMATION: Description of Unknown Organism: illustrative
      DNA sequence

<400> SEQUENCE: 2
ttgttcgcct gaccacaccc gtgccgctcc ggttggccga ctcactgcgc gtcttctgtc        60
ccgccctacc tctcgttcca tagttagcat cgcttgcgta tccttcatgt ttgattcgat       120
cttactttat attgtacgtt atgcacattt ttctactcgg tccagcctag cttaattcaa       180
tctcccttgg tttcgtgtat ttagtctgcc atccgtcacc tgttgctcta tcattacccc      240
acttcctcag ttcttttgtc g                                                 261